United States Patent [19]

Keppel et al.

[11] Patent Number: 5,734,066
[45] Date of Patent: Mar. 31, 1998

[54] SUPRESSION OF AUTOIGNITION IN MALEIC ANHYDRIDE PRODUCTION

[75] Inventors: Robert A. Keppel, Chesterfield; Scott F. Mitchell, St. Charles; Michael J. Mummey, Foley, all of Mo.

[73] Assignee: Huntsman Petrochemical Corporation, Austin, Tex.

[21] Appl. No.: 835,152

[22] Filed: Feb. 13, 1992

[51] Int. Cl.$^6$ .................................................. C07D 307/60
[52] U.S. Cl. .................................................. 549/259
[58] Field of Search .............................. 427/239; 549/259

[56] References Cited

U.S. PATENT DOCUMENTS

| | | | |
|---|---|---|---|
| 4,596,878 | 6/1986 | Click et al. | 549/259 |
| 5,117,007 | 5/1992 | Taheri et al. | 549/259 |

FOREIGN PATENT DOCUMENTS 54-46713  4/1979  Japan .

OTHER PUBLICATIONS

Jost, Explosion and Combustion Processes in Gases, McGraw–Hill, pp. 185–188 (1946).

*Primary Examiner*—Bernard Dentz
*Attorney, Agent, or Firm*—Senniger, Powers, Leavitt & Roedel

[57] ABSTRACT

An improved process for the manufacture of maleic anhydride by catalytic oxidation of n-butane in which the feed flow channel to the catalytic reactor contains an autoignition suppression agent containing acid sites or trivalent phosphorus as an ignition inhibiting component. The autoignition suppression agent may also be used in other gas/liquid containment envelopes for flammable mixtures of hydrocarbons and oxygen. A novel apparatus and method are disclosed for assessing the influence of system conditions on autoignition of hydrocarbon/oxygen mixtures.

13 Claims, 11 Drawing Sheets

TYPICAL PLOT OF PRESSURE AND TEMPERATURE DATA OBTAINED IN THE STATIC AIT SYSTEM

ACTIVATION PLOT FOR A CARBON STEEL VESSEL

5,734,066

SUPRESSION OF AUTOIGNITION IN MALEIC ANHYDRIDE PRODUCTION

BACKGROUND OF THE INVENTION

This invention relates to a method and apparatus for determining the autoignition conditions of flammable mixtures and to methods for controlling autoignition in such mixtures. More particularly, the invention relates to an improved process for the manufacture of maleic anhydride from n-butane and air or oxygen at high productivity using flammable n-butane/air or oxygen mixtures, without autoignition of the feed mixture.

In the manufacture of organic oxygen compounds by controlled partial oxidation of hydrocarbons in the presence of a catalyst, maximum productivity and optimum economic operation often require the use of flammable feed mixtures of hydrocarbon and air or other source of oxygen. If such feed compositions are exposed to a source of ignition, combustion, sometimes explosive combustion, can result in the reactor or reactor feed system with consequent loss of yield and productivity. Even in the absence of an extraneous ignition source, flammable mixtures of hydrocarbon and air or oxygen are subject to autoignition if exposed to elevated temperatures and pressures for a sufficient period of time for an oxidation chain reaction to develop. Whether resulting from autoignition or an extraneous ignition source, explosive combustion of the hydrocarbon feed mixture not only creates a loss in productivity but may be a hazard to equipment integrity and personnel safety.

Autoignition is usually reported in the literature in the form of temperature. The reported autoignition temperature (AIT) of a flammable gas is the lowest temperature at which a given flammable gas will self-ignite, for a given set of process conditions. This value, once determined, is used to set the maximum upper limit operating temperature for a process operated under a particular combination of hydrocarbon concentration and pressure. Because AIT tends to decrease with increased pressure, it operates as a constraint on the optimization of the productivity of processes such as catalytic oxidation of n-butane to maleic anhydride or the catalytic oxidation of p-xylene to phthalic anhydride.

However, to determine the AIT of a flammable mixture in a specific process is not a straightforward task. Autoignition is dependent not only on the conditions at which a process is operated, but also on such factors as the size and shape of the vessel. As indicated above, many of the conditions at which the process runs, i.e., pressure, concentration of flammables, and residence time can have a direct impact on the value reported for an AIT. These factors, combined with the fact that laboratory autoignition data cannot be scaled up to determine the AIT of a process vessel of interest, leads to the conclusion that the AIT of a given process vessel is unique and can only be determined via experimentation with that vessel.

In view of these considerations, it might seem fruitless to conduct laboratory scale experimentation for the determination of AIT. However, due to both economic and safety constraints, laboratory experimentation is usually the only avenue available. Most laboratory AIT work reported in the literature is conducted in static flow glass systems at atmospheric pressure. In fact, all standardized test procedures prescribe the use of atmospheric pressure. However, this type of testing is of little use in determining AITs in a commercial maleic anhydride process because the operating pressure of such process is significantly higher than that prescribed by standardized test methods. This problem is aggravated by the established commercial need to operate at progressively higher pressures to achieve maximum productivity of the maleic anhydride reactor.

For example, in many commercial maleic anhydride reactors operated by applicants' assignee, operating pressures have been progressively increased over a period of several years from the neighborhood of below 20 psig to 30 psig and above, and the butane concentration has been increased from about 1.7% by volume up to about 2.4% by volume. As the severity of the process conditions is increased, so is the potential for autoignition of the feed mixture in the feed flow channel to the catalytic reactor. Thus, a need has arisen for the development of methods for determining the effect of process variables on autoignition and for developing means for controlling autoignition in the reactor system, especially in the feed flow channel to the reactor.

Autoignition of flammable mixtures may also be of concern in the carburetion systems of internal combustion engines as well as the carburetion systems of gas-fired or oil-fired furnaces and boilers. Problems may also occur in the vapor space of atmospheric storage tanks containing flammable liquids. Although temperatures in such tanks are generally modest, it is known that autoignition temperatures are inversely related to vessel size. Thus, very large storage tanks for flammable liquids may create an autoignition hazard even under ambient storage conditions. Even where autoignition as such is not a risk, the presence of pyrophors may induce ignition at low temperature under certain conditions of pressure and concentration. A further need has remained in the art for determining the susceptibility of flammable mixtures to ignition in the presence of pyrophors.

SUMMARY OF THE INVENTION

Among the several objects of the present invention, therefore, may be noted the provision of a method for the determination or estimation of the autoignition temperature of a flammable mixture; the provision of such a method which determines the relative influence of the pressure, concentration, volume, and other conditions on the autoignition temperature of a flammable mixture; the provision of an apparatus for estimating autoignition temperatures and determining the effect of system variables on autoignition; the provision of a method to suppress autoignition in n-butane/air or oxygen mixtures utilized in the manufacture of maleic anhydride; the provision of methods for the suppression of autoignition in hydrocarbon/air or oxygen mixtures generally; and the provision of a method for preventing the ignition of flammable mixtures by pyrophors.

Briefly, therefore, the present invention is directed to an improvement in a process for the manufacture of maleic anhydride by catalytic oxidation of n-butane over a vanadium phosphorus oxide catalyst. The process comprises mixing n-butane with an oxygen-containing gas and passing the resulting mixture over the catalyst in a catalytic reaction zone. The improvement comprises mixing n-butane and air in a reactor feed flow channel to produce a mixture containing at least about 1.7% by volume n-butane at a pressure of at least about 20 psig. The feed flow channel contains an autoignition suppression agent in contact with the mixture. The autoignition suppression agent comprises acid sites or trivalent phosphorus as an ignition inhibiting component.

The invention is further directed to a process for applying an autoignition suppression agent to a wall of the feed flow channel through which a feed mixture containing a hydrocarbon and oxygen can be introduced into a reactor. The process comprises mixing n-butane and an oxygen containing gas in the said feed flow channel to produce a gas mixture containing at least about 1.7% by volume n-butane at a pressure of at least about 20 psig. While n-butane and air are being mixed in the channel, a phosphate or phosphite ester is introduced into the feed flow channel under such conditions that the ester deposits in a coherent condensed state on the wall of the feed flow channel. The ester is maintained in contact with oxygen and a source of iron at said wall at a temperature sufficient to cause decomposition of the ester and formation on the wall of a polyphosphate polymer containing acid moieties or trivalent phosphorus as an ignition inhibiting component.

The invention is further directed to a process for applying an autoignition suppression agent to a wall of a containment envelope for a flammable mixture containing a hydrocarbon and a source of oxygen. A wall of the containment envelope is contacted with a phosphate or phosphite ester in the absence of the flammable mixture and under such conditions that the ester deposits in a coherent condensed state on the wall. The ester is maintained in contact with oxygen and a source of iron at the wall at a temperature of at least about 80° C. for a time sufficient to cause decomposition of the ester and formation on the wall of a polyphosphate polymer containing acid moieties or trivalent phosphorus as an ignition inhibiting component.

The invention is further directed to an improvement in a process for the manufacture of maleic anhydride by the catalytic oxidation of n-butane. In the process, a vapor containing n-butane is generated by vaporizing a liquid hydrocarbon mixture containing n-butane and higher boiling hydrocarbons, mixing the n-butane containing vapor with air and the passing the resulting mixture over a catalyst in a catalytic reaction zone. In accordance with the improvement, higher boiling hydrocarbons of the hydrocarbon mixture are separated from n-butane to produce a refined n-butane vapor containing at least about 96.2% by volume n-butane. The refined n-butane vapor is mixed with an oxygen containing gas in a feed flow channel for the reactor, thereby producing a feed mixture containing n-butane and oxygen which is introduced into the reactor. Thus, autoignition of the feed mixture is suppressed by controlling the proportion of higher boiling hydrocarbons in the feed mixture.

Further included in the invention is an improvement in the immediately aforesaid process which comprises passing n-butane containing vapor through a filter effective for removal of pyrophoric solids entrained in the vapor. Ignition of the mixture thus suppressed by eliminating a source of ignition.

Further included in the invention is an apparatus for determining the conditions of autoignition of flammable mixtures containing hydrocarbons and oxygen. The apparatus comprises: a furnace; means for controlling the temperature within the furnace; within the furnace, a cell comprising a pressure vessel in which autoignition of flammable mixtures of hydrocarbons and oxygen may be induced; an inlet line for introducing a hydrocarbon and oxygen into the cell; an isolating valve in the inlet line which may be closed to isolate a hydrocarbon/oxygen mixture in the cell for determining its autoignition temperatures; means for sensing the temperature in the cell; means for sensing the pressure in the cell; means in communication with the temperature sensor for recording temperatures as a function of time; means in communication with the pressure sensor for recording pressure as a function of time; and computer means in communication with the temperature sensor, the pressure sensor, and the isolating valve. The computer comprises means for generating a signal for transmittal to the isolating valve to close the valve.

The invention is further directed to a method for determining the autoignition conditions for a flammable mixture containing hydrocarbon and oxygen. In accordance with the method, the hydrocarbon and the gas containing oxygen are introduced into a test cell pressure vessel having walls constituted of thermally conductive material. The cell is maintained in an environment, the temperature of which is controlled at a predetermined temperature or in accordance with a predetermined temperature schedule. The pressure of the gas contained in the cell is sensed and the pressure within the cell is recorded as a function of time. Autoignition of the mixture is determined as a function of time, temperature, and pressure.

Other objects and features will be in part apparent and in part pointed out hereinafter.

DESCRIPTION OF PREFERRED EMBODIMENT

In accordance with the invention, an apparatus and method have been developed for determining the influence of system parameters on the autoignition of hydrocarbon/air or other hydrocarbon/oxygen mixtures. Although the apparatus and method are not adapted to predict the absolute values of the variables or combinations of variables that result in autoignition in a commercial scale operation, the influence of particular variables may be reliably identified. It has been found that the relative influence of operational variables as identified using the apparatus and method of the invention is readily translatable to a commercial system containing mixtures of the hydrocarbons with oxygen.

Figure 1:
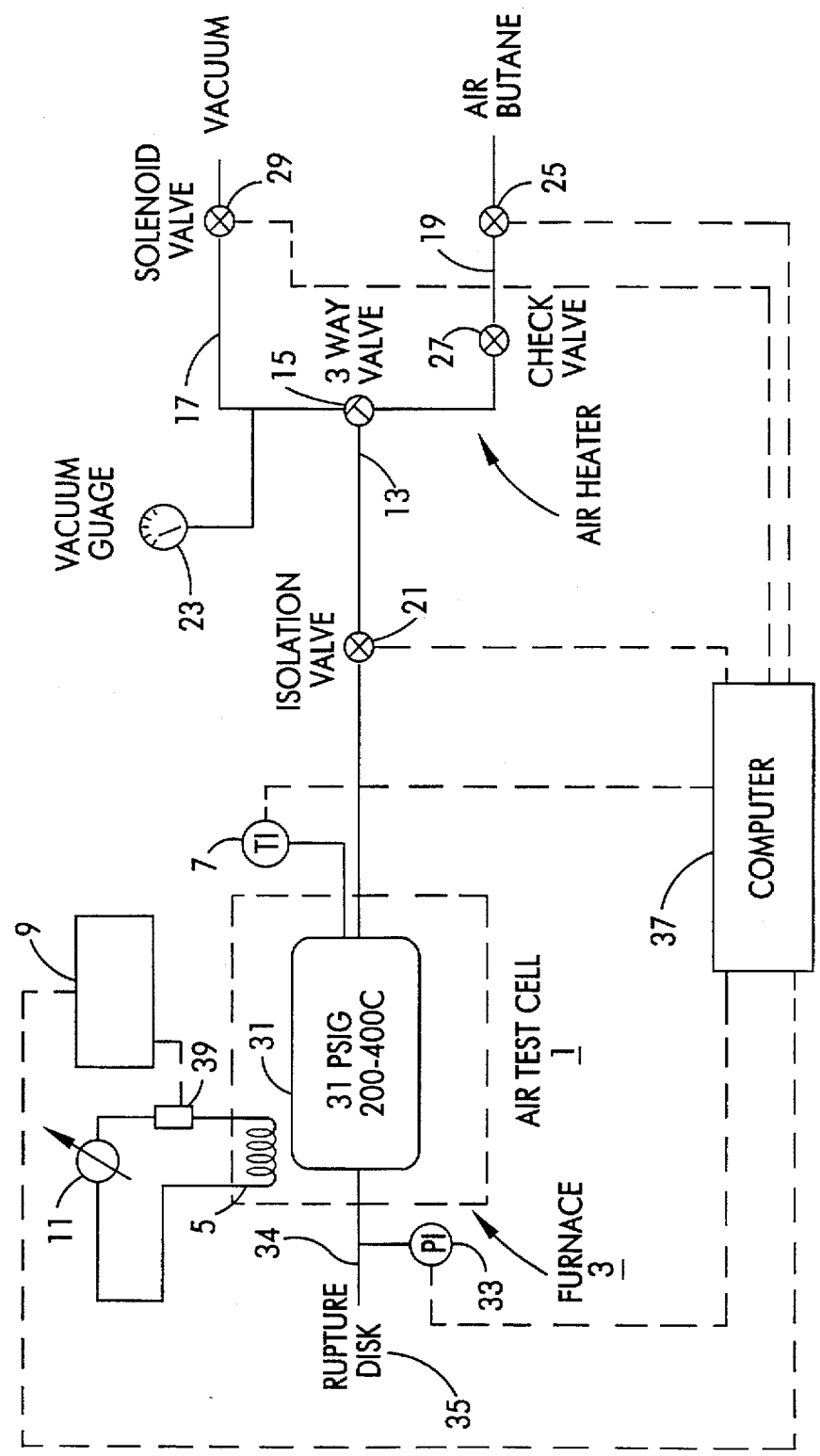
FIG. 1 is a schematic illustration of an apparatus of the invention for determining autoignition temperature and assessing the effect of system variables on autoignition.

The static flow autoignition test apparatus is illustrated in FIG. 1. A test cell 1, comprising a pressure vessel rated at 1800 psi and constructed of thermally conductive material, such as 304-L stainless steel, is contained within a furnace 3. The interior of furnace 3 is heated by a resistance coil 5 to which current is supplied by a power source 11 through a relay 39. The skin temperature of the test cell within the furnace is sensed by a temperature sensor 7 which is in communication with a temperature recorder controller 9. Temperature controller 9 in turn communicates with relay 39, rapidly cycling the relay on and off to control the time average power supply to coil 5, and thereby maintain the temperature within the furnace at a desired level or in accordance with the desired schedule.

A pipeline 13 connects cell 1 to one port of a three-way solenoid valve 15, the other two ports of which are connected to sources of air and hydrocarbon through a line 19 and to a vacuum through a line 17. Between valve 29 and valve 15 in line 17 is a 0-25 psia vacuum gauge 23. Between valve 15 and cell 1 in line 13 is an isolation valve 21. Between the air/butane sources and valve 15 in line 19 are a solenoid valve 25 and a check valve 27. Between the vacuum source and valve 15 in line 17 is a solenoid valve 29.

A thermocouple 31 serves as a temperature sensor for the gas contained in cell 1. A pressure sensor 33 communicates with a line 34 between cell 1 and rupture disk 35. In order to avoid errors in pressure measurement resulting from gas flow pressure drop during the initial filling of the vessel, the connection between test cell 1 and line 34 is remote from the connection between the test cell and line 13, preferably on the opposite side of the cell. Both thermocouple 31 and pressure sensor 33 communicate with a computer 37. Computer 37 may also communicate with temperature controller 9 to control the temperature within furnace 3 at a predetermined level in accordance with a predetermined schedule. The computer also correlates the pressure and temperature within cell 1 as measured by sensors 33 and 31, respectively, as a function of time and provides a record of temperature versus time and pressure versus time, preferably in the form of two dimensional plots. Additionally, the computer also communicates with solenoid valve 15, isolation valve 21, solenoid valve 25 and solenoid valve 29, sending signals to open or close these valves at programmed pressures and times.

In the method of the invention for determining the autoignition conditions for a particular air and hydrocarbon mixture, cell 1 is first evacuated by instructing computer 37 to open isolation valve 21, align three-way solenoid valve 15 to connect lines 13 and 17, and open solenoid valve 29 to connect cell 1 to the vacuum source. After evacuation is complete, as indicated by vacuum gauge 23, isolation valve 21 is closed. Next, the three-way valve 15 is operated to connect lines 19 and 13 preparatory to introduction of the air/hydrocarbon mixture into cell 1. Before flow of air and hydrocarbon is initiated, the temperature controller 9 is programmed to establish a predetermined test temperature in test cell 1 by adjustment of variable voltage source 11.

Except upon the occurrence of a thermal event inside the cell, the thermal conductivity of the wall of cell 1 assures that the temperature inside the cell is identical to the temperature within furnace 3 to ±3 ° C. Once the desired initial temperature has been reached in furnace 3, solenoid valve 25 and isolation valve 21 are operated to admit air and hydrocarbon into the cell via lines 19 and 13. A flammable mixture of a predetermined composition is admitted into the test cell, causing the pressure in the cell to rise progressively. Computer 37 is programmed to allow introduction of oxygen/hydrocarbon mixture until a predetermined test pressure has been reached. Using the apparatus of the invention, autoignition tests may be run at pressures significantly removed from atmosphere, for example, at a fill pressure of 15 psig and above, or a vacuum of 10" Hg or greater. When the test pressure is sensed by sensor 33, the computer sends a signal to close isolation valve 21 and solenoid valve 25. Meanwhile, the temperature within furnace 3 is controlled according to the schedule desired for the test. In order to obtain meaningful and reliable data, the temperature in furnace 3 is preferably maintained constant, not only throughout the filling cycle, but throughout the entire duration of the test. After the desired pressure is reached, temperature and pressure are both maintained constant until autoignition is detected.

Computer 37 provides a recording of pressure as a function of time, preferably in the form of a two-dimensional plot. Autoignition is indicated by a sharp and rapid increase in pressure. Thus, the pressure versus time record provides a measure of induction time for autoignition at the test temperature and filling pressure. A plot of temperature versus time provides corroboration of the point at which autoignition occurs, but the best measure of induction time is the pressure versus time plot since it indicates the time between attainment of the test pressure and detection of autoignition.

The test apparatus and method of the invention can be utilized to determine the effect of numerous variables in a particular operation that utilizes flammable mixtures of hydrocarbons and oxygen. The method is especially advantageous for providing information on the variables affecting autoignition in a feed system for a catalytic oxidation reactor, for example, in the preparation of maleic anhydride by oxidation of n-butane or the preparation of phthalic anhydride by oxidation of p-xylene. However, the apparatus and method can also be used to determine the effect of operational variables in other systems such as, for example, the carburetion system for an internal combustion engine. Among the variables whose influence can be measured are temperature, pressure, composition of the mixture, and materials with which the flammable mixture comes in contact, for example, the materials of construction of the feed channel through which the flammable mixture flows on its way to the catalytic reactor or internal combustion engine. As noted above, no absolute prediction can be made of the combination of temperature, pressure, composition, and materials of construction which will result in autoignition in the commercial system of interest. However, by running autoignition tests which vary one parameter while holding the others constant, the influence of that parameter on autoignition can be determined. The sensitivity of autoignition to the test parameter as determined in the test apparatus and method is reliably translatable to a commercial system even though the absolute value of that parameter at which autoignition will occur cannot be predicted from the test results, even where other parameters are fixed.

As discussed above, it is well known that the autoignition temperature varies inversely with the size of the vessel or chamber in which autoignition occurs. This point is readily demonstrated by using test cells of different size in the test apparatus of FIG. 1. Additionally, however, the test apparatus and method can be used to determine the effect of factors such as vessel shape and especially surface to volume ratio on the autoignition of particular flammable mixtures.

In accordance with the improved process of the invention for the manufacture of maleic anhydride, it has been determined that, by use of an autoignition suppression agent, a catalytic reactor may be operated under increasingly severe pressure and concentration conditions to produce maleic anhydride at high productivity without suffering autoignition (over-pressure) events. Conventionally, maleic anhydride is produced by the catalytic oxidation of n-butane over a vanadium/phosphorus oxide catalyst. n-Butane is mixed with air and the resulting mixture is passed over the catalyst in a catalytic reaction zone in which the n-butane substrate undergoes a controlled oxidation to maleic anhydride. In the process of the invention, n-butane and air are mixed in a reactor feed flow channel that contains an autoignition suppression reagent in contact with the n-butane/air mixture. Ordinarily, the catalytic oxidation is carried out in a fixed bed tubular reactor, advantageously, the tubes of a shell and tube heat exchanger. A cooling fluid, typically a salt bath, is circulated through the shell of the heat exchanger to remove the heat of reaction. Air and n-butane are mixed in the inlet head of the shell and tube reactor or in a pipeline or mixing chamber immediately upstream of the inlet head. In such a system, the feed flow channel includes the inlet head and any portion of the system upstream of the head through which the n-butane/air mixture passes.

When a maleic anhydride reactor is operated in previously conventional conditions, for example, at n-butane concentrations of up to about 1.7% by volume and total pressure below about 18 psig, the incidence of autoignition in the reactor or its feed flow channel is very low. However, as the severity of reaction conditions is increased, over pressure events—which indicate autoignition—occur with sharply increasing frequency. Thus, the provision of an autoignition suppression reagent becomes desirable at combination of n-butane concentration greater than about 1.7% by volume, and total pressure greater than about 20 psig. For a maleic anhydride reactor inlet head having a surface to volume ratio of about 7 $m^{-1}$ or lower, the autoignition suppression method of the invention is of increased significance at combinations of n-butane concentration greater than about 1.7% and total pressures greater than about 23 psig. In a system having such a surface to volume ratio, the method is especially valuable at combinations of n-butane concentration greater than about 1.7% and total reactor pressure greater than about 28 psig. By use of the improved process of the invention, successful operation has been demonstrated at n-butane concentrations in the range of 2.4% and total pressures in the range of 31 psig.

In a reactor feed channel or chamber systems having a surface to volume ratio lower than 4 $m^{-1}$, a significant incidence of autoignition events may occur at pressures as low as 20 psig or lower. Moreover, if the n-butane source is contaminated with as much as about 2% or more of pentane or other higher boiling hydrocarbons, autoignition may occur at pressures below 20 psig even if the surface to volume ratio of the inlet feed channel is greater than 7 $m^{-1}$. The method of the invention is effective and significant for the suppression of autoignition in such systems. The method makes possible operation of high capacity reactors having a high inlet head volume at unprecedented combinations of pressure and concentration.

Preferably, the autoignition suppression agent is present as a coating on the inside wall of the feed flow channel. Advantageously, the entire wall surface of the head and other components of the feed flow channel are coated with the autoignition suppression agent. This includes the inside wall of the head itself, the tube sheet facing the head, and pipeline surfaces and any mixing chamber upstream of the head. However, it is not critical that the autoignition suppression agent entirely coat all of these wall surfaces. The autoignition suppression agent does not function negatively to prevent contact between the n-butane/air mixture and the wall but instead functions positively, by itself contacting the n-butane/air mixture.

For use in a maleic anhydride reactor feed channel, the autoignition suppression agent should be effective at temperatures up to about 450° C. It has been found that a coating containing trivalent phosphorus or free acid moieties is operationally stable and effective in inhibiting autoignition at temperatures up to 450° C. Preferably, therefore, the suppression agent comprises a polyphosphate ester polymer which contains trivalent phosphorus or free acid sites, more preferably both trivalent phosphorus and free acid moieties. It has been found that such a suppression agent can be produced in situ on the inside wall of the feed flow channel of a maleic anhydride reactor. Under similar conditions, a polyphosphate ester suppression agent can be produced in other systems. This suppressant composition contains at least about 1 wt % trivalent phosphorus, typically about 1% to about 38%, preferably about 13% to about 29%. Alternatively, where water vapor is present, the composition may have a molar ratio of phosphorus to oxygen ("P/O") between that of 100% phosphoric acid (0.25) and that of phosphorus pentoxide (0.4). Where the air/hydrocarbon mixture contains water vapor, a polyphosphate ester polymer having a P/O ratio in this range hydrolyzes to provide free acid sites in a proportion sufficient to inhibit autoignition. For this purpose, the water content of the hydrocarbon air mixture should be be such that the dew point of the mixture is between about −15° C. and about 40° C. Most preferably, the suppressant agent comprises both trivalent phosphorus and a 0.272 to 0.4 P/O polyphosphate ester polymer. Under such conditions, the frequency of acid sites is between about 0.07 and about 3.0, preferably between about 1 and about 2.3, per phosphorus atom (or per repeating unit of the polyphosphate).

It will be understood that, while the polyphosphate material described above has proven especially advantageous, particularly in a maleic anhydride manufacturing operation, acidic materials other than polyphosphates can be used as autoignition suppressants. For example, gamma-alumina, zeolites and other solid phase acid materials may be used. The frequency or density of acid sites necessary to provide effective suppression can be generally determined from the frequency described above with respect to the polyphosphate suppression agent.

In accordance with the method of the invention for imparting autoignition suppressant properties to a maleic anhydride feed flow channel, a phosphate or phosphite ester is introduced into the flow channel under such conditions that it deposits in a coherent condensed state on a wall of the feed flow channel. For example, it may simply be introduced as a liquid through an open-ended feed tube. It preferably is not introduced as a finely atomized spray, all the droplets of which may be carried through the feed channel in the gas stream. At least a portion of the ester deposited on the wall decomposes to produce a decomposition product that polymerizes to form the polyphosphate ester polymer. For the decomposition and polymerization reaction to take place at a reasonably rapid rate, it has been found that a phosphite ester deposited on the feed channel wall must be at a temperature of at least about 80° C., and a phosphate ester must be at a temperature of at least about 105° C., in the presence of both oxygen and an active source of iron. Where the feed channel is constructed of carbon steel, iron from the steel wall is available to catalyze the formation of the polyphosphate ester. In this instance, it is preferable that the wall temperature also be above about 80° C. or 105° C. since reaction is believed to take place essentially at the wall surface. Although the conditions of formation of the polyphosphate ester polymer are not highly critical, it is preferred that the temperature be in the range of between about 150° C. and about 200° C. under an oxidizing environment.

In a maleic anhydride manufacturing plant, an autoignition suppression agent may be applied by this method during the course of normal operations, avoiding the need for a shutdown of the plant. However, the utility of the polyphosphate ester agent is not limited to maleic anhydride reactor feed systems. By introducing a phosphate or phosphite ester under the temperature and oxidizing conditions outlined above, a polyphosphate ester containing trivalent phosphorus and having the desired P/O ratio may be applied to the inside wall of a hydrocarbon liquid storage vessel, carburetion system or other containment envelope for flammable mixtures in which autoignition risks prevail. Thus, a liquid hydrocarbon storage vessel, process vessel, combustion chamber, or other gas and liquid containment envelope may be provided with an autoignition suppression agent prior to the introduction of hydrocarbon liquid and, thus, in the absence of a flammable mixture. In such applications, the conditions of deposition conditions may be more closely controlled than in the in situ deposition in a maleic reactor head, though the latter method is advantageous for existing maleic plants where deposition of the suppression agent may be accomplished without significant downtime. In either method of deposition of the suppressant agent, the active iron source is preferably a wall of the containment envelope. It will be understood that the term wall refers broadly to any surface with which the gas may be in contact within the envelope, and may include a baffle, tray or other surface to which the polyphosphate ester may be applied. Advantageously, the autoignition suppression agent is applied to the wall of the vessel or chamber by introducing the phosphate or phosphite ester into in the envelope in a manner comparable to that described above for a maleic anhydride reactor. Alternatively, however, a baffle tray, or other wall component of the containment envelope may be pre-treated to deposit the autoignition suppressant thereon before such component is incorporated into the vessel or chamber.

It has further been discovered that autoignition of industrial grade n-butane/air mixtures may be minimized, i.e., the AIT increased, by controlling to a minimum the proportion of higher boiling hydrocarbons in the n-butane/air mixture. In a conventional process for the manufacture of maleic anhydride by catalytic oxidation of n-butane, a vapor containing n-butane is initially generated by vaporizing a liquid hydrocarbon mixture containing n-butane, the n-butane containing vapor is then mixed with air, and the resulting air/hydrocarbon mixture is passed over a vanadium/phosphorus oxide catalyst in a catalytic reaction zone. In the commercial operation of this process, the n-butane-containing vapor and, therefore, the n-butane/air mixture, are commonly contaminated by higher boiling hydrocarbons contained in the liquid mixture, especially pentane.

Figure 11:
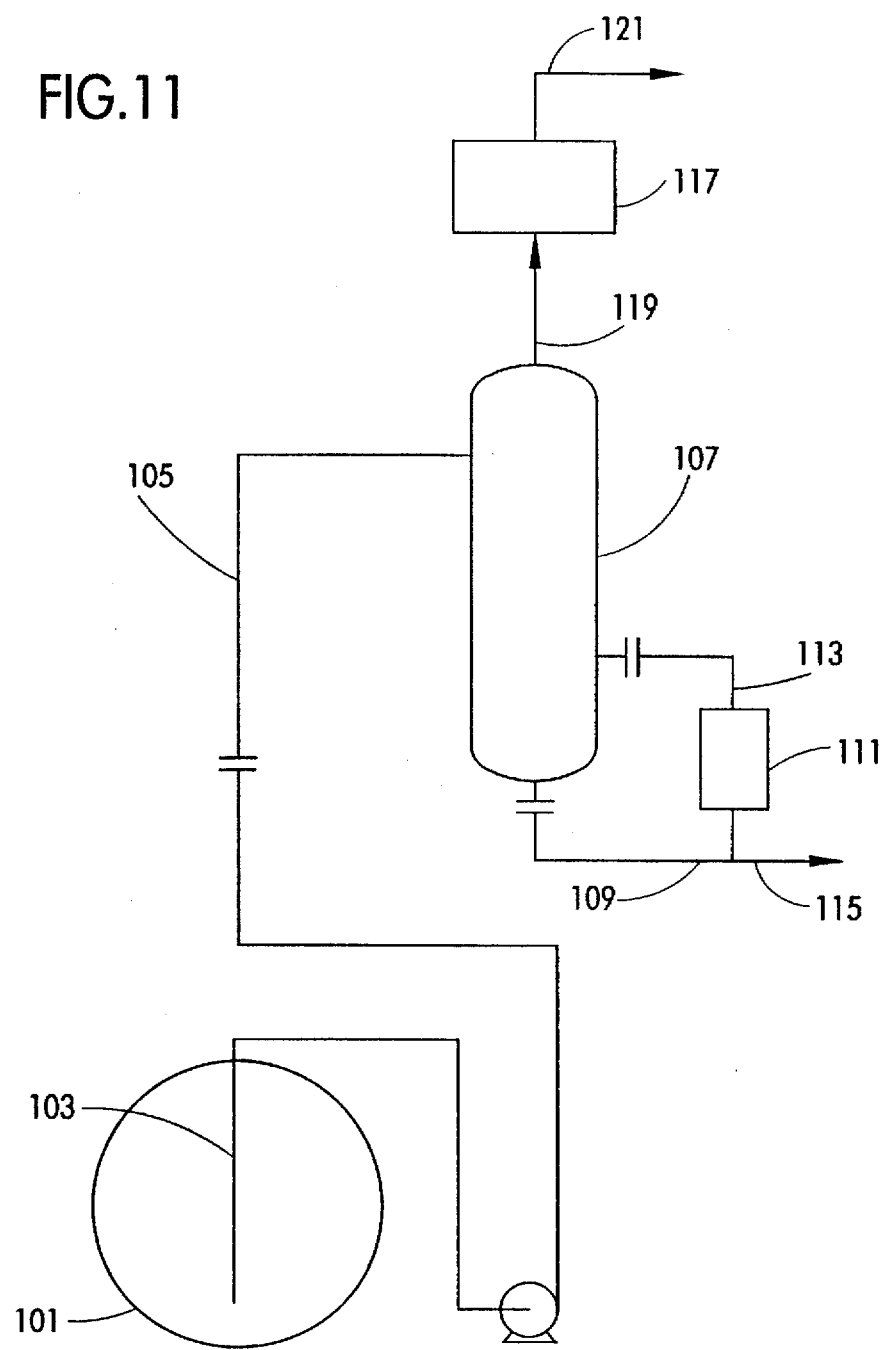
FIG. 11 is a schematic illustration of a system for controlling to a minimum the high boiling components of an n-butane containing vapor produced by evaporation of a liquid hydrocarbon mixture.

It has been found that the presence of significant concentrations of pentane tends to lower the autoignition temperature of n-butane/air mixtures. Industrial grade n-butane is often contaminated with 0.5% to 2.0% by weight pentane, and may contain only 95.5% by weight n-butane. In accordance with the invention, autoignition is inhibited by separating pentane and other higher boiling hydrocarbons from the n-butane-containing vapor used to prepare the n-butane/air mixture. This is effected by fractionating the hydrocarbon mixture, preferably by stripping n-butane from higher boiling hydrocarbons in the liquid mixture. Illustrated in FIG. 11 is an apparatus effective for producing an n-butane vapor containing a minimum proportion of higher boiling hydrocarbons. Shown at 101 is a liquid hydrocarbon reservoir comprising a pressure storage vessel. A standpipe 103 in vessel 101 connects to a feed pump 104 which is in turn connected to a stripping column 107 through a feed line 105. Feed line 105 connects at the first tray or stage at the top of the column. A bottoms liquid line 109 connects the bottom exit of the column to the inlet of a thermosiphon reboiler 111, and a line 113 connects the exit of the reboiler to the bottom tray or stage of the column. Typically, the fractionation system, including column 107 and reboiler 111, contains at least about seven theoretical trays or equilibrium stages. A line 115 provides for removal from the system of column bottoms flowing in line 107. The top of column 107 is connected to a vapor filter 117 through a a vapor line 119. Filter 117 contains woven element's having an average pore size effective to remove particles having a dimension of 25 microns or greater, preferably 10 microns or greater. Filter 117 is connected to the inlet of a maleic anhydride reactor (not shown) via a reactor feed line 121.

If the filtered gas comes in contact with active iron under anaerobic conditions, further iron sulfides may form by reaction of iron with any hydrogen sulfide that may be contained in the gas. Accordingly, the housing of filter 117, any other components of the filter which come into contact with the refined n-butane vapor, and reactor feed line 121 should be constructed of a material which does not have active iron at its surface in contact with the gas. Stainless steel is preferred. Alternatively, the filter housing or pipeline may be lined with a Teflon or other coating that does not contain active iron. Once the n-butane has been mixed with air, the presence of oxygen inhibits the formation of iron sulfides.

In operation of the system of FIG. 11 according to the method of the invention, pump 104 is operated to feed liquid hydrocarbon contained in vessel 101 through line 105 to column 107. In the column the hydrocarbon liquid mixture is fractionated by stripping the n-butane from higher boiling hydrocarbons. Where the liquid hydrocarbon fed to the column is industrial grade n-butane having the composition described above, refined n-butane vapor leaving the column through line 119 has an n-butane content of at least about 96.2% by weight, preferably at least about 96.6% by weight, and a pentane content of no greater than about 0.58% by weight, preferably no greater than about 0.45% by weight. Liquid flowing out of the bottom of the column is divided, about 99% flowing through reboiler 111 where it is revaporized for return to the column through line 113. The remainder of the bottoms liquid is removed from the system via line 115 and directed to a waste gas flare for disposal. The liquid hydrocarbon stripping system may be operated over a range of head pressures, and is advantageously operated at a pressure sufficiently higher than the operating pressure of the maleic anhydride reactor to allow for regulated flow of n-butane into the reactor feed channel. Alternatively, the process may be operated at reduced pressure, with a compressor being provided to charge the refined n-butane vapor to the reactor.

Further in accordance with the invention, it has been discovered that pyrophors commonly present in n-butane oxidation systems may be entrained in the n-butane vapor and induce ignition in the feed flow channel of a maleic anhydride reactor. In particular it has been found that particulate iron sulfide can cause such ignition events. Generally, pyrophoric effects are experienced from iron sulfide particles only where the iron sulfide is present in a particle size greater than about 75 microns. However, in operation of a maleic anhydride reactor system, it has been found that iron sulfide particles having a size as low as about 10 microns may induce ignition, with particles of 25 to 50 microns or greater having a substantial pyrophoric effect. In an improved process of the invention, this source of ignition of the feed mixture is eliminated by passing the n-butane vapor through a filter effective for removal of pyrophoric solids, especially iron sulfides. It has been found that a woven fabric filter medium effective to remove particles having a dimension less than about 25 microns is effective for this purpose. Preferably, the filter medium is effective for removal of 10 micron particles, more preferably 5 micron particles. A preferred filter element is comprised of a cellulose fiber having a melamine or other amine aldehyde resin coating. Where the n-butane source hydrocarbon mixture is fractionated, the filter is preferably placed in the exit vapor line from the fractionation column, as shown, for example, in FIG. 11.

The following examples illustrate the invention.

EXAMPLE 1

Figure 2:
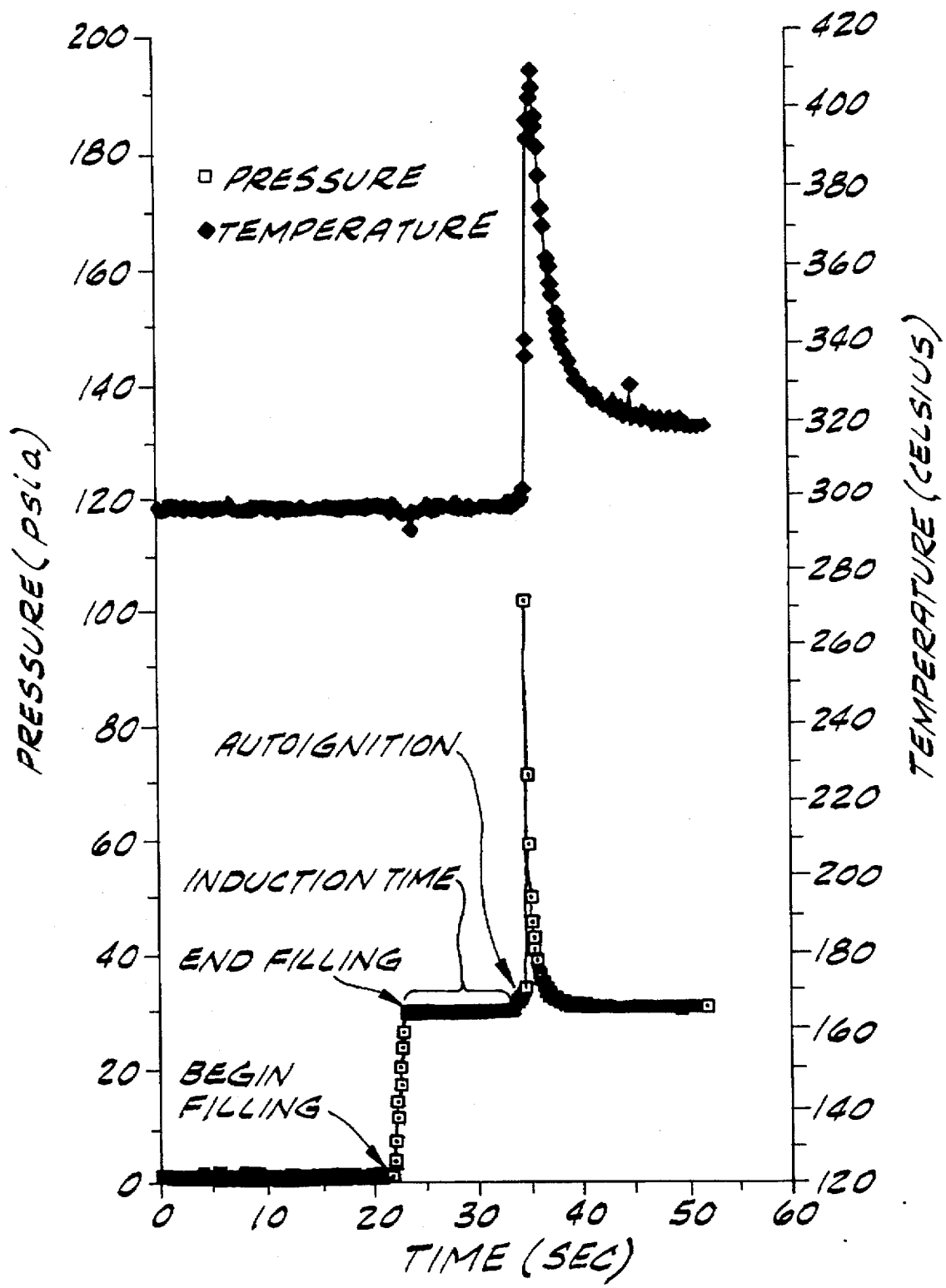
FIG. 2 is a plot of temperature and pressure as a function of time as produced by the computer component of FIG. 1 in determination of the autoignition temperature of an n-butane/air mixture.

A static flow test cell contained in an apparatus of the type illustrated in FIG. 1 was evacuated and then filled to a pressure of 31 lbs. per square inch gauge with a mixture of 2.4% by volume n-butane in air. The test cell had a volume of 1000 cc and the environment surrounding the test cell in the furnace was maintained at a constant temperature of 293° C. during the filling operation and thereafter until autoignition. Both temperature and pressure within the cell were measured and recorded as a function of time. These plots are set forth in FIG. 2, which indicates that the induction time for autoignition after filling of the test cell was approximately sixteen seconds.

Figure 3:
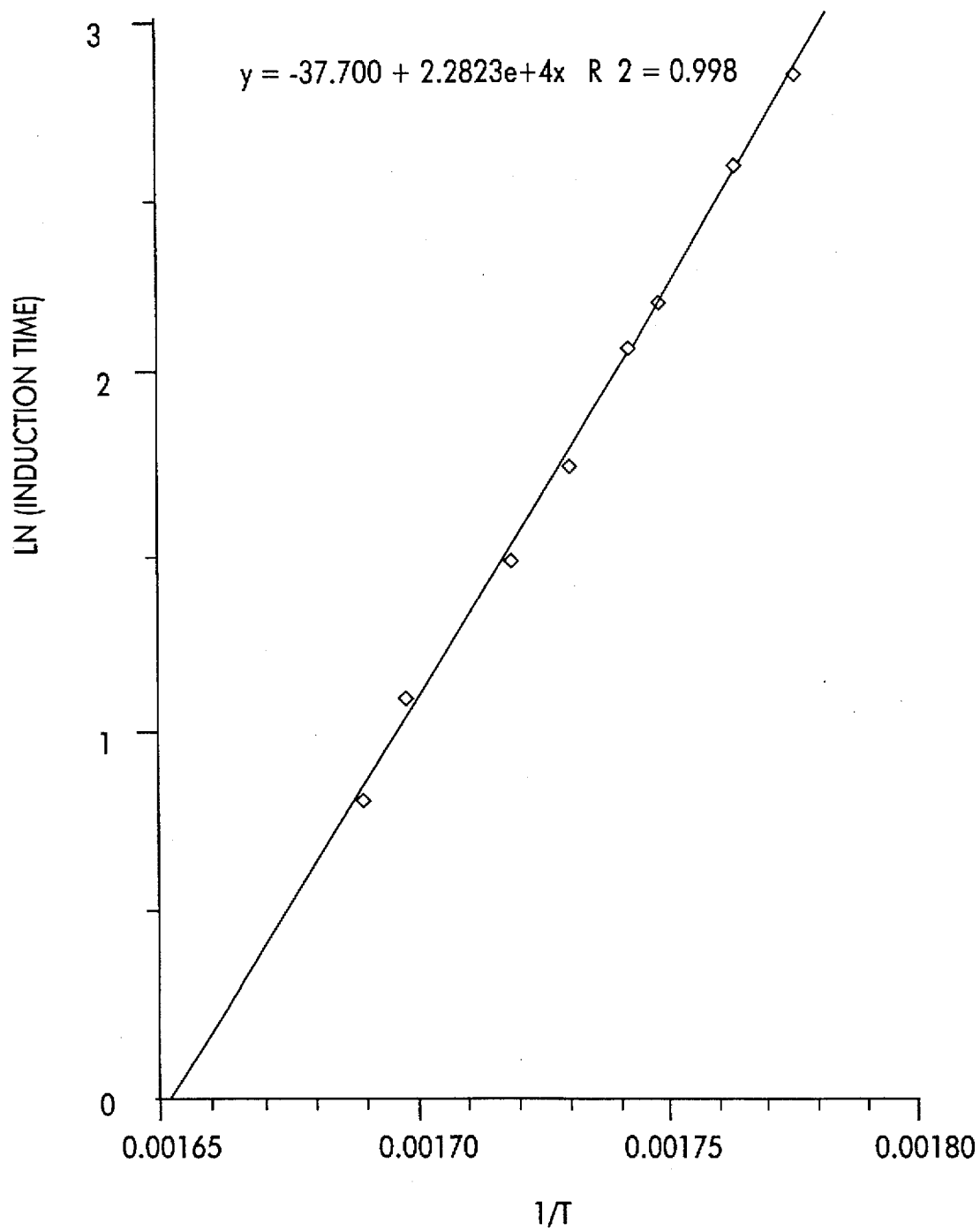
FIG. 3 is a plot of the natural logarithm of induction time vs. reciprocal of absolute temperature for a series of determinations of autoignition of 2.4% by volume n-butane in air mixtures at nominally 31 psig at different test temperatures, obtained by use of the apparatus of FIG. 1.

A series of tests were run according to the method described above, varying only the temperature of the gas within the cell prior to autoignition. Control of this temperature was effectively accomplished by programming temperature controller 9 to control the temperature within furnace 3. Prior to autoignition, the skin temperature of the cell varied by no more than ±3° C. along the length of the cell. Data from these tests was correlated by plotting the log of induction time against the reciprocal temperature. This plot is set forth in FIG. 3. It may be seen that it follows the Semenov equation almost exactly. From the slope of the curve, the apparent activation energy can be determined.

EXAMPLE 2

Figure 4:
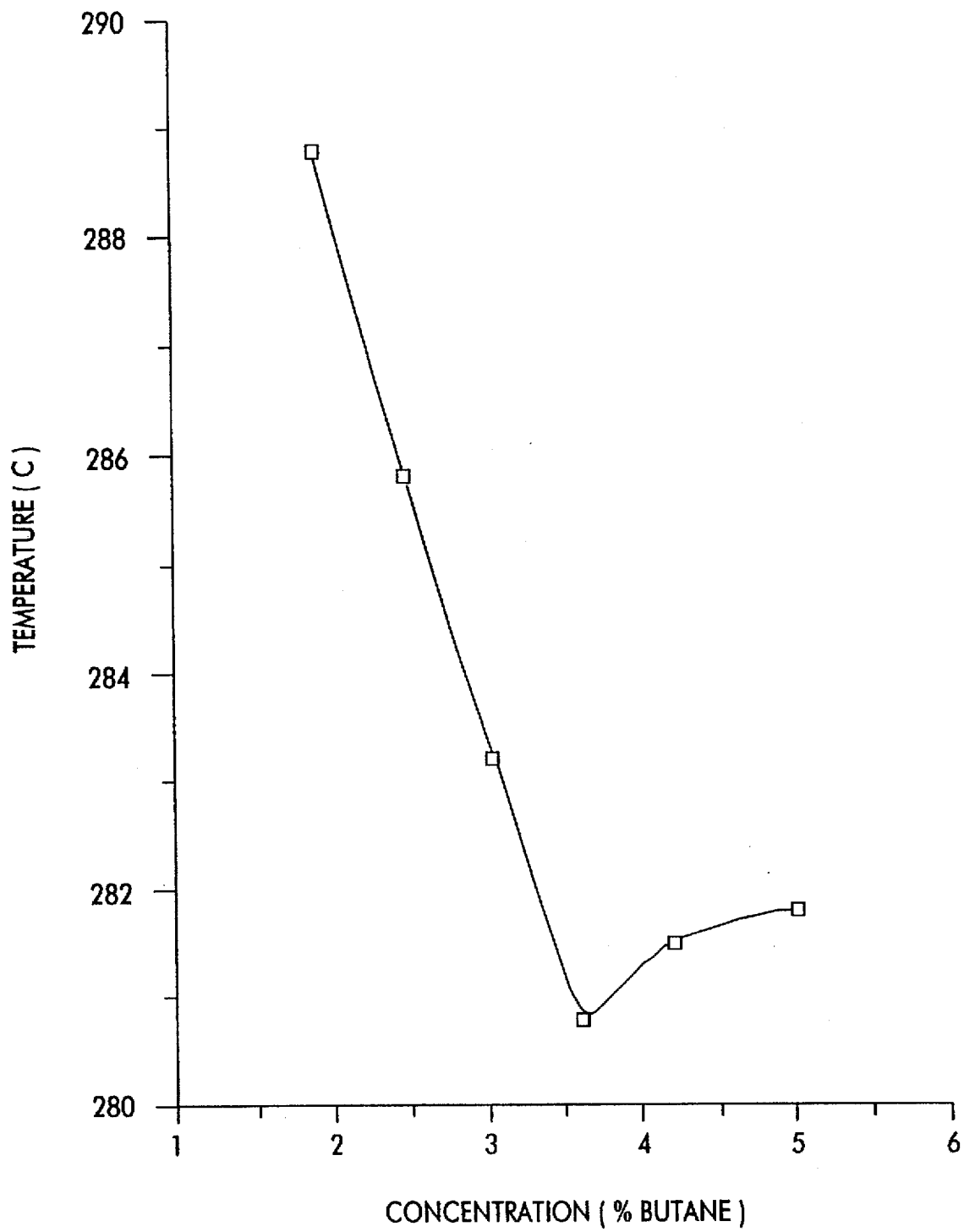
FIG. 4 is a plot of temperature vs. n-butane concentration for a series of determinations of the autoignition temperatures of nibutane/air mixtures of varying concentration at 31 psig, obtained with the apparatus of FIG. 1.

Using the apparatus and method of Example 1, tests were run to determine the autoignition temperature of n-butane/air mixtures at 45 psia total pressure and butane concentrations ranging from 1.8% to 5.0%. For purposes of the tests of this example, the autoignition temperature was arbitrarily determined to be the temperature at which autoignition occurred after an induction time of about 15–25 seconds following filling of a 1000 cc test cell to a pressure of 45 psia. The results of the tests of this example are set forth in FIG. 4.

The tests of this example determined the effect of varying the relative concentrations of n-butane and air at a fixed pressure.

EXAMPLE 3

Using the apparatus and method of Example 1, tests were conducted to determine the effect of total pressure on the autoignition temperature of mixtures of 2.4% by volume n-butane in air. Thus, the tests of this example determined the effect of absolute n-butane and air concentrations at fixed relative concentrations of 2.4% n-butane whereas the tests of example 2 determined the effect of varying relative n-butane and air concentrations at fixed total pressure.

Figure 5:
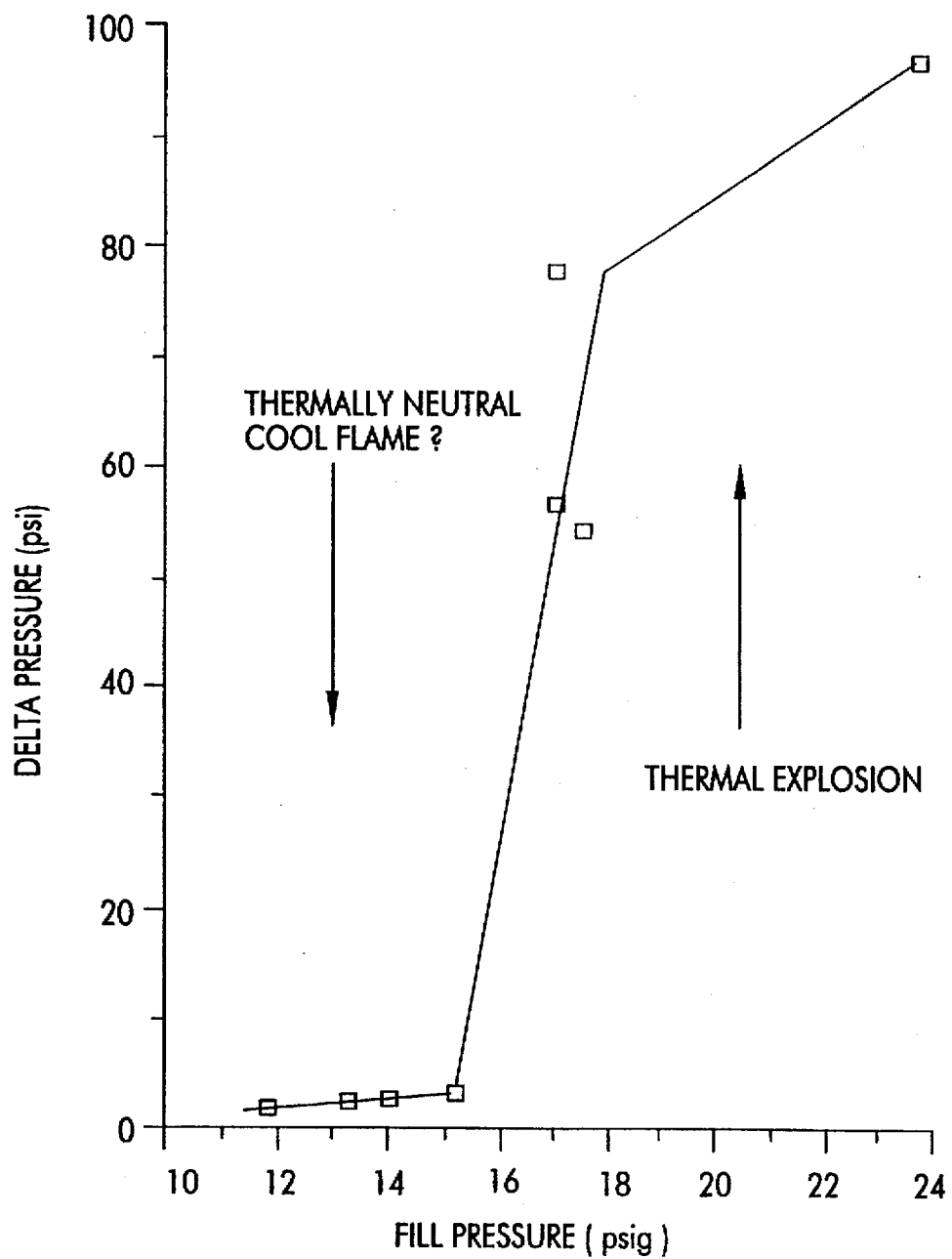
FIG. 5 is a plot of pressure increase vs. fill pressure for a series of autoignition determinations for 2.4% by volume n-butane in air mixtures at 290° C. using the apparatus of FIG. 1.

The tests of this example were all conducted at a furnace temperature of 290° C. Set forth in FIG. 5 is a plot of the maximum change in pressure recorded after filling the vessel versus the initial fill pressure of a 1000 cc test cell. The results of this test indicate that the transition to combustion or autoignition is markedly affected by the total number of moles of butane and oxygen in the vessel, (i.e., the pressure). A significant finding of the data of this example is the shape of the curve of FIG. 5, which indicates that the response of autoignition to pressure is very sharp and that a change of a few pounds operating pressure can determine whether or not a combustion event will occur.

EXAMPLE 4

Using the methods and apparatus generally described in Example 1, the effect of various impurities was determined for mixtures of 2.4% by volume n-butane in air. A number of compounds were chosen as representative of impurities which had been identified in the feed to a commercial maleic anhydride manufacturing plant. These included various organosulfur compounds such as ethyl disulfide, methyl sulfide, ethanethiol, methyl disulfide, and hexanthiol.

Tests were also conducted with pentane as representative of higher hydrocarbons with which the n-butane source may be contaminated. In both tests, autoignition temperature was determined as a function of total pressure, with autoignition temperature being defined as the temperature at which autoignition is observed after an induction time of 15–25 seconds in a 1000 cc test cell.

Figure 6:
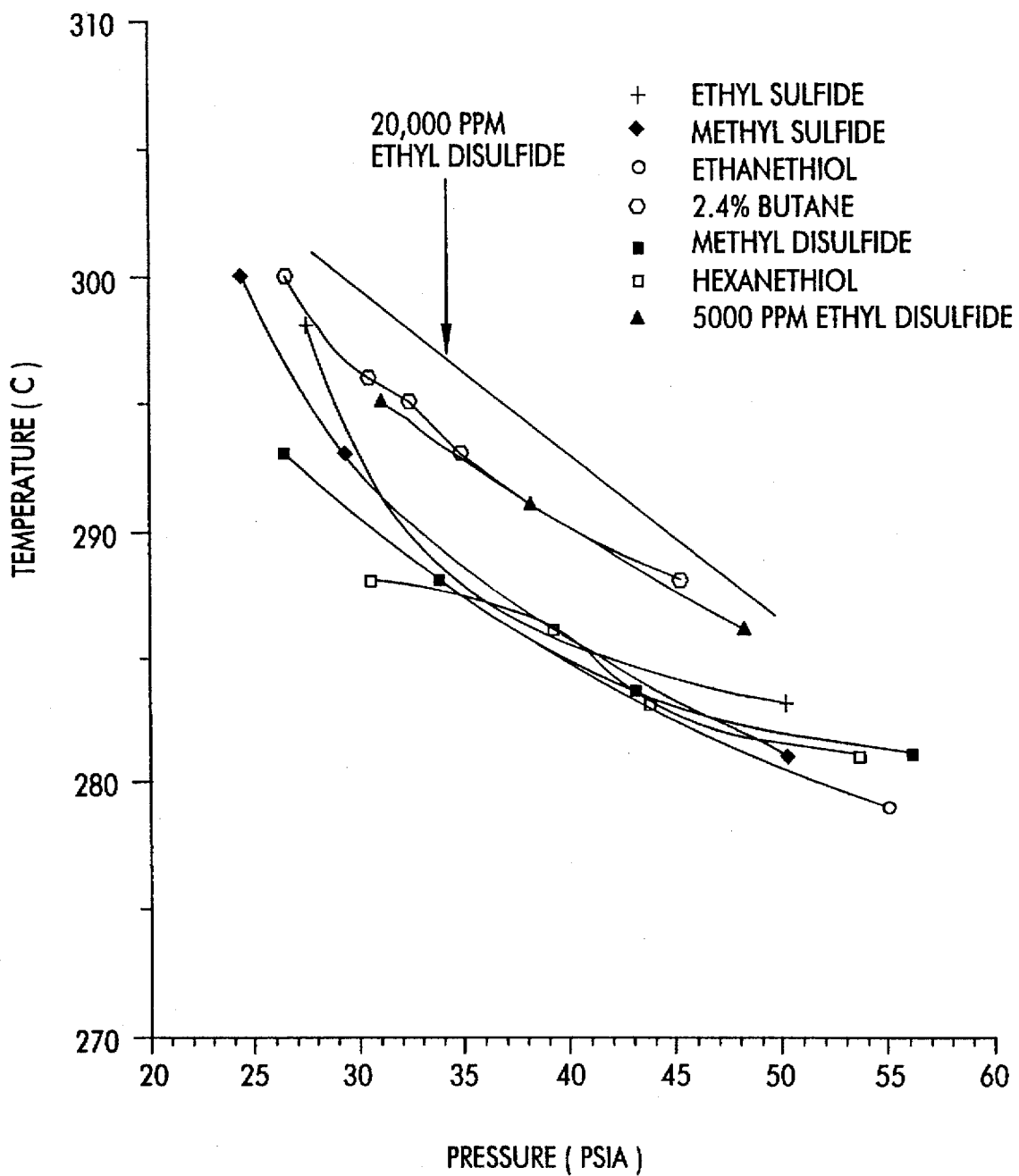
FIG. 6 is a series of plots of autoignition temperature vs. fill pressure for 2.4% by volume n-butane in air mixtures containing indicated concentrations of organosulfur compound contaminants.
Figure 7:
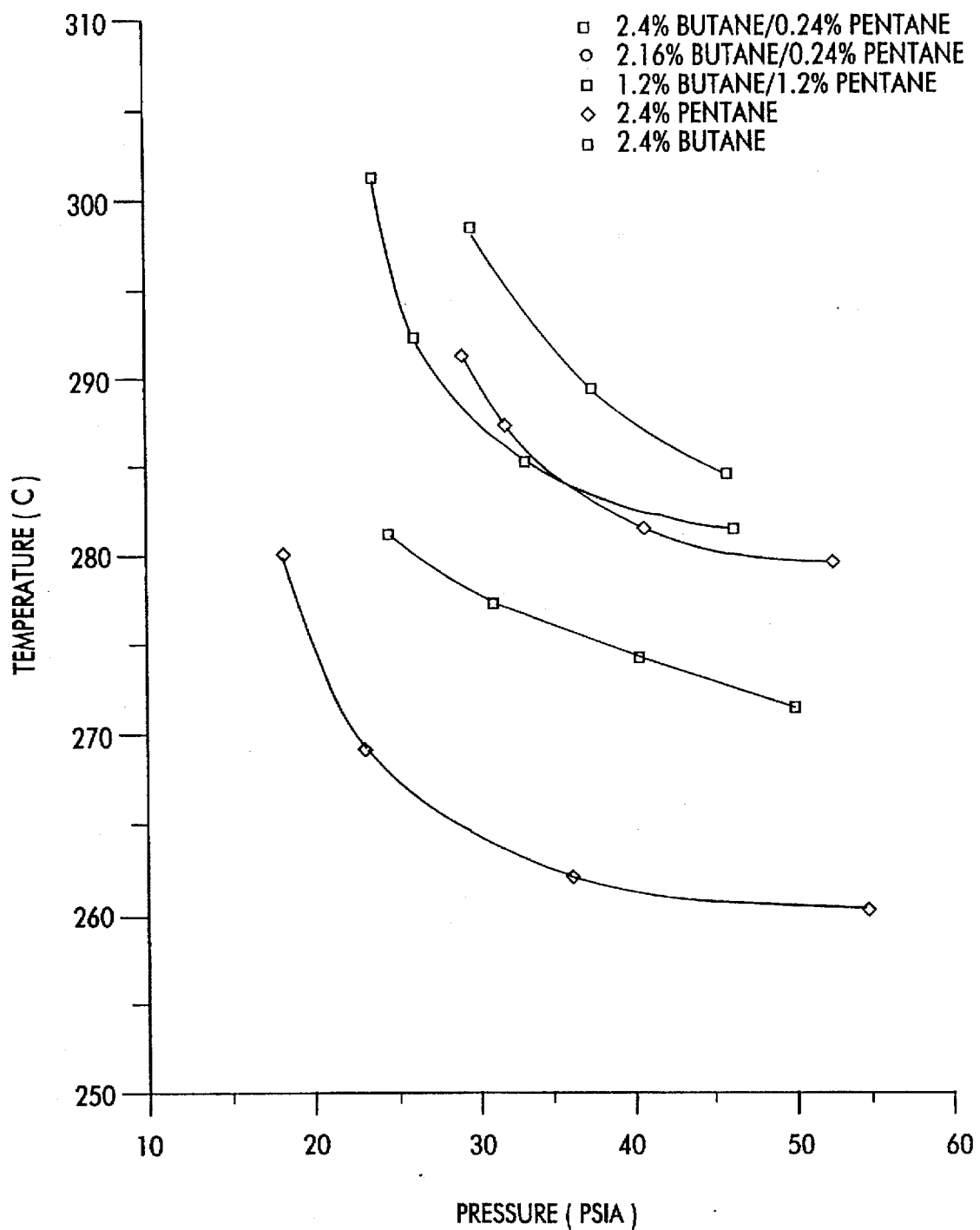
FIG. 7 is a series of plots illustrating the relationship between autoignition temperature and fill pressure for various mixtures of air with n-butane, pentane, and mixtures thereof.

The results of the tests of this example are set forth in FIGS. 6 and 7. The results of this example indicate that organosulfur compounds appear to have a very small effect on autoignition temperature over the concentration range studied. Substantial concentrations of pentane, on the other hand, were observed to have a significant effect on the autoignition temperature.

EXAMPLE 5

Using the methods and apparatus of Example 1, tests were conducted to identify possible ignition sources within a commercial maleic anhydride plant which could cause ignition at a temperature below the autoignition temperature of the flammable n-butane/air mixture fed to the maleic anhydride reactor. One candidate for study was the springs used in the bottom tube sheet of the commercial reactor to hold the catalyst in place. The other was pyrophors, possibly present in the butane vaporizer for the plant, especially iron sulfide type pyrophors. To study the effect of spring wire on autoignition temperature, various samples of wire were obtained from a spring manufacturer and placed inside the test cell. No observable affect on autoignition temperature was observed due to the presence of the wire.

Figure 8:
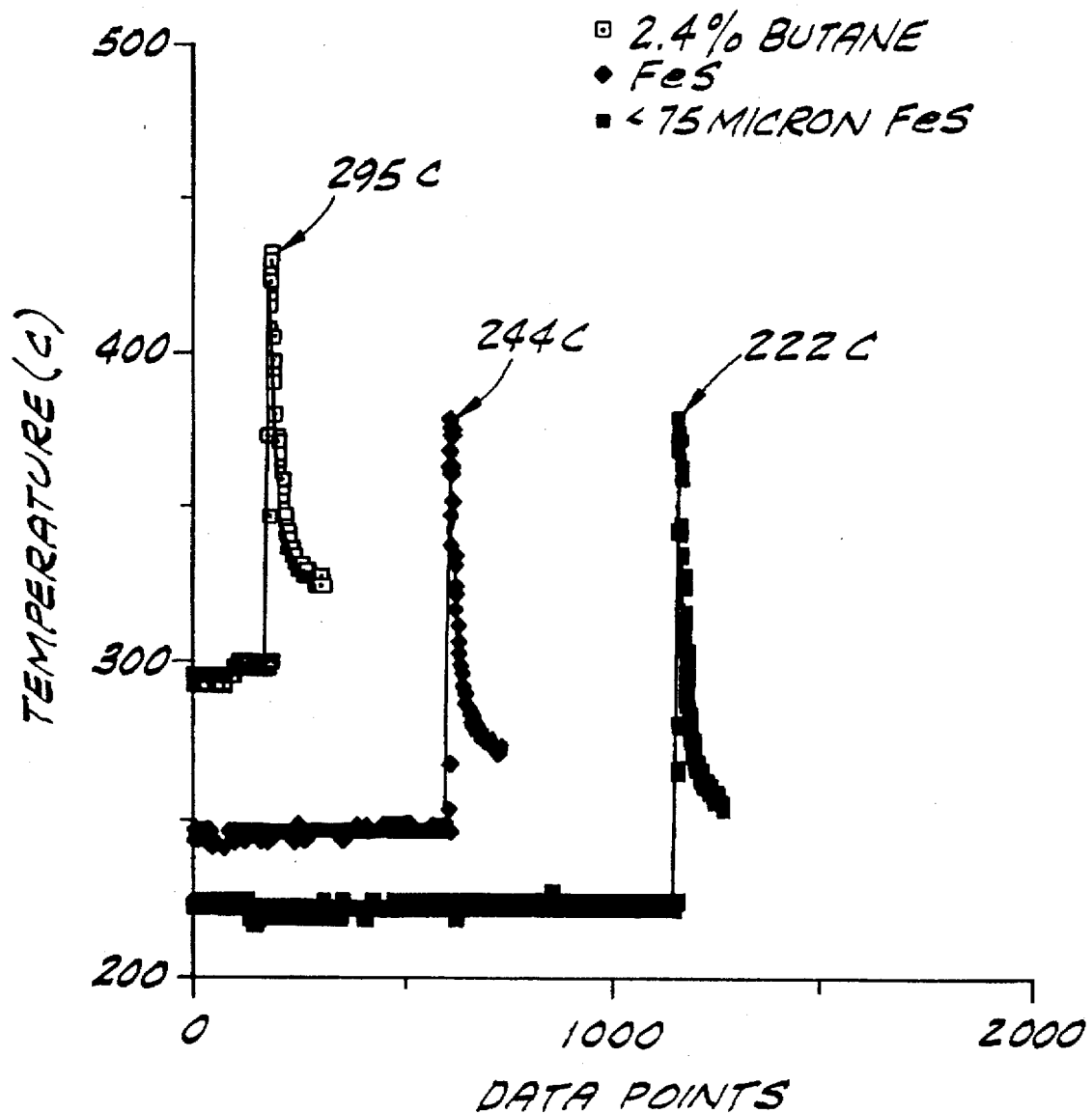
FIG. 8 is a plot produced by the computer component of FIG. 1 illustrating the effect of pyrophors on the autoignition temperature of 2.4% butane in air mixtures at an absolute pressure of 31 psi.

Since iron sulfide is solid, a method was developed to disperse particulate iron sulfide in the gas entering the test cell. Induction times were observed for autoignition at 31 lbs. per square inch absolute using a mixture containing 2.4% by volume n-butane in air in a 1000 cc test cell. The results of the tests of this example are set forth in FIG. 8.

EXAMPLE 6

Using the method and apparatus described in Example 1, tests were conducted to determined the effect of surface to volume ratio on autoignition temperature. Tests conducted with test cells of varying volume ranging from 80 cc to 1,000 cc confirmed the expected inverse relationship between volume and autoignition temperature. The results of these tests are set forth in Table 1.

TABLE 1

| Vol (cc) | Pressure (psig) | Temperature (°C.) | Shape |
| --- | --- | --- | --- |
| 1000 | 45 | 288 | Cylinder |
| 750 | 45 | 283 | Sphere |
| 80 | 52 | 400 | Cylinder |

Further tests were conducted in which a 80 cc test cell was filled with quartz wool in an amount sufficient to reduce the test cell volume by about 33% and dramatically increase the surface to volume ratio for the vessel. Tests were conducted at a series of combinations of temperature and pressure and no evidence of autoignition was observed even at extreme conditions of 76 psia and 402° C. This data suggests that the suppression of autoignition is far more effective than would be expected by a simple reduction in volume. This result demonstrates that the shape of the volume enclosed by the vessel (i.e., surface to volume ratio) also plays a major role in autoignition. More particularly, as surface to volume ratio increases, autoignition temperature also increases substantially.

EXAMPLE 7

Using the apparatus and method of Example 1, tests were conducted to identify materials which might either catalyze or inhibit autoignition. From the literature, it was known that the presence of certain metals can have a catalytic effect in initiating an autoignition. A postulation was made that, if autoignition could be catalytically initiated, it might also be catalytically inhibited. Numerous materials were tested for their effect on autoignition behavior.

Tests were first conducted varying the material of construction of the test cell. The materials tested were carbon steel and 304 stainless steel. Silver was also tested, in the form of an internal coating deposited from a colloidal dispersion of silver. No catalytic or inhibitory affect was noted for either 304-L or carbon steel. Silver caused a slight decrease in autoignition temperature.

Figure 9:
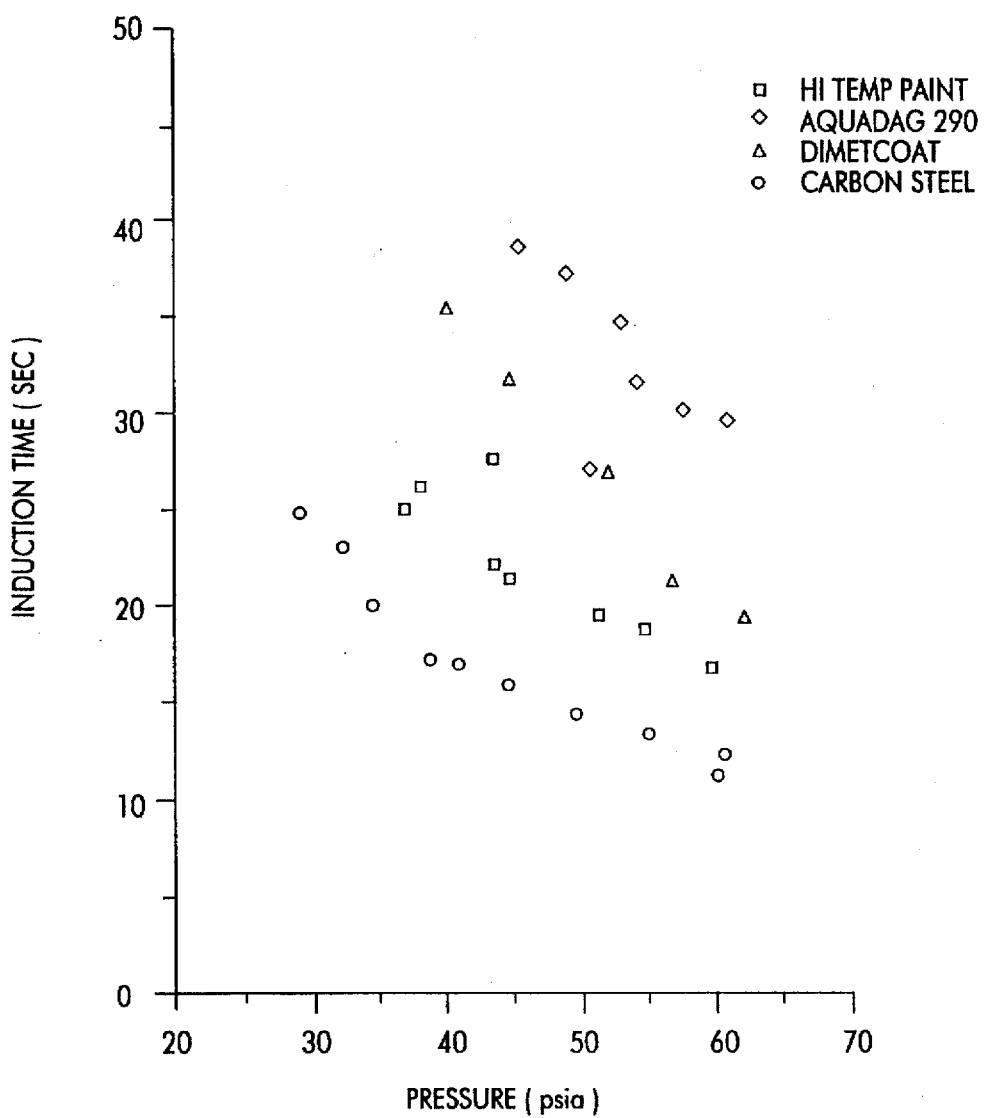
FIG. 9 is a plot of induction time to ignition vs. pressure for 2.4% by volume n-butane in air mixtures in a test cell coated with various autoignition suppression agents.

Next, tests were conducted to determine the effect of various coatings on autoignition. These included a colloidal graphite dispersion sold under the designation "Aquadag" by Acheson Colloids Co., high temperature paints, metal oxide paints, and zeolite materials. Induction time to autoignition was determined as a function of fill pressure for mixtures of 2.4% by volume n-butane in air at 290° furnace temperature. The results of the tests of this example are set forth in FIG. 9 for a high temperature paint comprising an epoxy-based resin containing silica and titania, a zinc-oxide based paint sold under the designation "Dimetcoat" by Ameron, Aquadag 290, and carbon steel as a control. From these coatings, little benefit in the inhibition of autoignition was observed.

Zeolite coatings, such as those available from Union Carbide under the trade designation LZ-Y20 HY Zeolite, were found to be quite effective in inhibition of autoignition. It is believed that the effectiveness of zeolite is primarily attributable to the very large increase in surface area that is caused by the presence of the zeolite. Thus, the mechanism of inhibition by zeolite is considered to be primarily physical in nature and not attributable to chemical inhibition of the oxidation of butane. Although zeolite may be an effective autoignition suppression agent for mixtures of air and n-butane or other hydrocarbons, its value in a maleic anhydride manufacturing process may be limited because the zeolite would tend to become coated with residues from the air/butane mixture, resulting in a substantial reduction of surface area and loss of autoignition suppression properties. Zeolite may not, for example, be a candidate for application to the walls of the feed flow channel of a maleic anhydride process for purposes of suppressing autoignition. On the other hand, it may be feasible to place a charge of zeolite or other molecular sieve in the feed channel in such a manner that it can be readily replaced on a periodic basis as its surface area is reduced by deposit of residues from the process.

Further tests were conducted in which the interior of the test cell was coated with various phosphorus compositions. In the tests, test cells were coated with phosphoric acid solutions, iron phosphate or phosphorus (V) oxide ($P_2O_5$, $P_4O_{10}$ or simply phosphorus oxide), and phosphorus tar obtained from a process similar to that which is takes place in a commercial type reactor wherein, in order to enhance catalyst life, trimethyl phosphate is injected into the n-butane/air mixture entering the reactor. Where such process is conducted under the conditions described hereinabove, a tarry substance (phosphorus tar) builds up on the walls of the feed flow channel to the reactor tubes (i.e., the inlet head of the shell and tubes of the maleic anhydride reactor. Again, induction time was measured as a function of fill pressure for 750 and 1000 cc test cells in a furnace at a temperature of 290° C., using a mixture of 2.4% by volume n-butane in air. The results of these tests are set forth in FIG. 10 for phosphoric acid solutions, iron phosphate, and phosphorus tars. It was found that a weak (i.e., less than 100%) phosphoric acid solution is of no benefit in suppressing autoignition as compared with an uncoated vessel, and that iron phosphate was similarly ineffective. Higher concentrations of phosphoric acid (i.e., greater than or equal to 105%) did effectively inhibit autoignition but the results did not translate from the stainless steel test cell of FIG. 1 to a carbon steel vessel. This was because of chemical reaction between the phosphoric acid and the carbon steel. The reaction converted phosphoric acid into iron phosphate which, as noted, showed no discernible autoignition inhibiting properties.

Phosphorus oxide was found to be effective in suppressing autoignition, but phosphorus oxide readily sublimes at the temperatures of the inlet head of a maleic anhydride reactor. Thus, phosphorus oxide may be an effective autoignition coating for air/hydrocarbon mixtures in other contexts but is not commercially attractive for use in the feed flow channel of a maleic or phthalic anhydride reactor. In a maleic process, sublimation would result in both loss of autoignition protection in the reactor head and plugging of lines downstream of the reactor where temperatures are low enough for $P_2O_5$ to condense.

Figure 10:
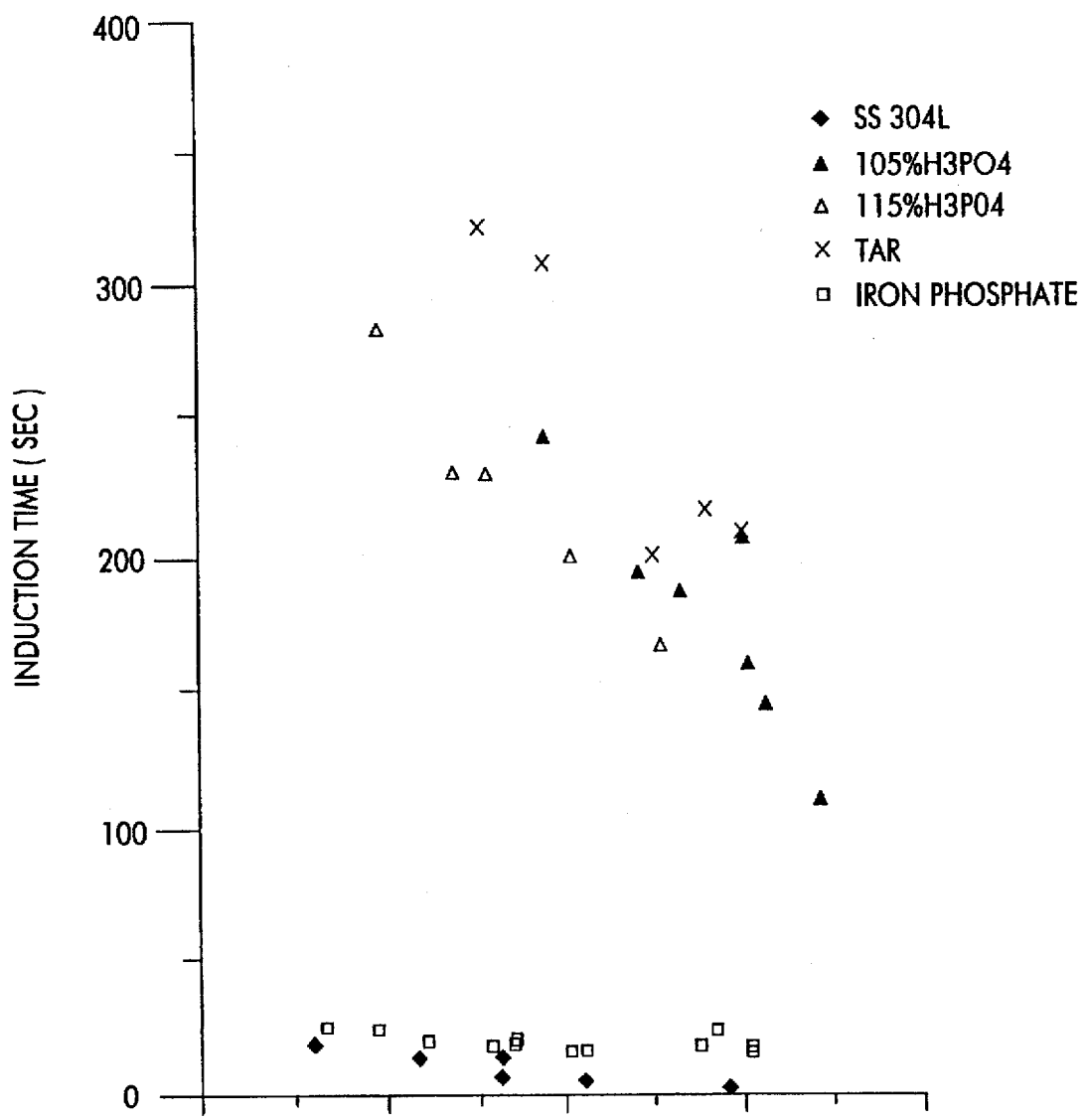
FIG. 10 is a series of plots of induction time to autoignition vs. pressure for 2.4% by voume n-butane in air mixtures in test cells of the type illustrated in FIG. 1, as interiorly coated with various phosphorus-containing coatings.

Tests of the phosphate tar, which was produced synthetically under the conditions describe above, demonstrated that this tar exhibits a substantial inhibitory effect. FIG. 10 shows that this material substantially increases the induction time for autoignition as compared to the results for an uncoated vessel. Moreover, it is not very chemically active towards carbon steel and, thus, remains stable and effective in a maleic anhydride reactor head.

EXAMPLE 8

Tests were conducted to determine whether the tar from a commercial type maleic anhydride reactor, which was determined in Example 7 to have a substantial autoignition suppressant effect, could be generated on a reproducible basis. It was postulated that this material is a polyphosphate ester formed by decomposition of the trimethylphosphate fed to the maleic anhydride reactor and polymerization of the decomposition product. Such material is non-corrosive to the carbon steel reactor. This tarry material is composed predominantly of phosphorus and oxygen and may contain a significant fraction of trivalent phosphorus.

In the investigation of the manufacture of the polyphosphate ester tar, experimental runs were made to determine the effectiveness of the following combinations of reaction conditions for generation of phosphorus-containing tar: (a) temperature only; (b) temperature and iron; (c) temperature and phosphorus oxide; and (d) temperature, iron, and air (or other oxygen source). These experiments demonstrated that only the combination of iron, heat, and air is sufficient to create the polyphosphate ester tars, and that this combination is effective to produce the tars on a reproducible basis. The particular conditions of tar formation are not narrowly critical, but is preferably at least about 80° C. for phosphite esters and at least about 105° C. for phosphate esters. Reasonably rapid formation of the tar is effected at a temperature in excess of about 125° C., preferably below about 200° C., under oxidizing conditions, with iron present in an active form so that it may effectively contact the reacting species. A carbon steel surface constitutes an effective iron catalyst but a stainless steel surface does not, presumably because of the presence of the protective oxide coatings of stainless steel. More particularly, it has been demonstrated that autoignition suppressant polyphosphate ester tar can be produced readily in situ in a maleic anhydride manufacturing plant from the phosphate ester that is otherwise injected into the process for the purpose of prolonging catalyst life. In this operation, it has been found that the phosphate ester should be deposited in a coherent condensed state on the iron surface, i.e., the wall of the feed flow channel to the reactor. Where, for example, the phosphate ester is fully atomized by discharging it through a metal frit into the n-butane feed line, the ester does not condense on the surface of the head, and polyphosphate ester tars are not generated in any useful quantity. On the other hand, where the phosphate ester is essentially dribbled into the air line to the head, it is maintained in a coherent condensed state so that it is deposited on the wall of the head, and over time a portion of the phosphate ester is converted in the presence of air and iron at a temperature greater than 125° C. to the polyphosphate ester tar. This tar is demonstrated to have effective autoignition suppressant properties.

As various changes could be made in the above methods without departing from the scope of the invention, it is intended that all matter contained in the above description and shown in the accompanying drawing shall be interpreted as illustrative and not in a limiting sense.

What is claimed is:

1. In a process for the manufacture of maleic anhydride by catalytic oxidation of n-butane over a vanadium/phosphorus oxide catalyst comprising mixing n-butane with an oxygen-containing gas and passing the resulting mixture over said catalyst in a catalytic reaction zone, the improvement which comprises:

mixing n-butane and air in a reactor feed flow channel to produce a mixture containing at least about 1.7% by volume n-butane at a pressure of at least about 20 psig, said feed flow channel containing an autoignition suppression agent in contact with said mixture, said autoignition suppression agent comprising an ignition inhibiting component selected from the group consisting of acid sites and trivalent phosphorus.

2. An improved process as set forth in claim 1 wherein said agent is stable at a temperature greater than about 450° C.

3. An improved process as set forth in claim 2 wherein said agent comprises a polyphosphate polymer containing trivalent phosphorus.

4. An improved process as set forth in claim 3 wherein said agent contains at least about 1% by weight trivalent phosphorus.

5. An improved process as set forth in claim 4 wherein the molar ratio of phosphorus to oxygen in said polyphosphate polymer is between about 0.25 and about 0.4, and the dew point of said mixture is between about −15° C. and about 40° C., whereby moisture in said mixture hydrolyzes said agent to provide acid sites in a concentration sufficient to suppress autoignition.

6. An improved process as set forth in claim 5, wherein said autoignition suppression agent is on an interior wall of said feed flow channel.

7. An improved process as set forth in claim 6 wherein said agent is deposited on said wall under oxidizing conditions by decomposition of a phosphate or phosphite ester introduced into said mixture and polymerization of the decomposition product to form said polyphosphate.

8. An improved process as set forth in claim 7 wherein phosphate or phosphite ester is introduced into said flow channel under such conditions that said ester deposits in a coherent condensed state on said wall, and phosphate or phosphite ester on said wall decomposes to produce the decomposition product which polymerizes to form said polyphosphate.

9. An improved process as set forth in claim 8 wherein said wall comprises iron in a form effective to catalyze the decomposition of said ester and the polymerization of said decomposition product.

10. An improved process as set forth in claim 9 wherein said wall comprises carbon steel.

11. An improved process as set forth in claim 9 wherein said wall has a surface temperature of at least about 80° C. where said ester is a phosphite ester and at least about 105° C. where said ester is a phosphate ester.

12. In a process for the manufacture of maleic anhydride by catalytic oxidation of n-butane over a vanadium/phosphorus oxide catalyst comprising mixing n-butane with air and passing the resulting mixture over said catalyst in a catalytic reaction zone, the improvement which comprises:

mixing n-butane and air in a reactor feed flow channel having a surface to volume ratio of not greater than about 4 m$^{-1}$ to produce a mixture containing at least about 1.7% by volume n-butane, said feed flow channel containing an autoignition suppression agent in contact with said mixture, said autoignition suppression agent comprising an ignition inhibiting component selected from the group consisting of acid sites and trivalent phosphorus.

13. In a process for the manufacture of maleic anhydride by catalytic oxidation of n-butane over a vanadium/phosphorus oxide catalyst comprising mixing n-butane with air and passing the resulting mixture over said catalyst in a catalytic reaction zone, the improvement which comprises:

mixing n-butane and air in a reactor feed flow channel to produce a mixture containing at least about 1.8% by volume n-butane and hydrocarbons having a boiling point higher than n-butane in a proportion of at least about 2% by volume based on n-butane content, said feed flow channel containing an autoignition suppression agent in contact with said mixture, said autoignition suppression agent comprising an ignition inhibiting component selected from the group consisting of acid sites and trivalent phosphorus.

* * * * *